United States Patent [19]

Stevens et al.

[11] Patent Number: 4,992,444
[45] Date of Patent: Feb. 12, 1991

[54] ANTIFOLATE AGENTS

[76] Inventors: Malcolm F. G. Stevens, 35 Chantry Road, Moseley, Birmingham B13 9DL; Roger J. Griffin, 36 Denewood Avenue, Handsworth Wood, Birmingham B20 2AB; Michelle A. Meek, 27 Hillaries Road, Erdington. Birmingham, B23 7OS, all of England

[21] Appl. No.: 127,452

[22] Filed: Dec. 2, 1987

[30] Foreign Application Priority Data

Dec. 2, 1986 [GB] United Kingdom ............... 8628731
Sep. 10, 1987 [GB] United Kingdom ............... 8721283
Sep. 10, 1987 [GB] United Kingdom ............... 8721284

[51] Int. Cl.$^5$ .................... A61K 31/505; C07D 239/48
[52] U.S. Cl. .......................... 514/275; 544/325
[58] Field of Search .................... 544/325; 514/275

[56] References Cited

U.S. PATENT DOCUMENTS 4,556,709 12/1985 Grohe et al. .

FOREIGN PATENT DOCUMENTS

84/04746 6/1984 PCT Int'l Appl. .
2158068 6/1985 United Kingdom .

OTHER PUBLICATIONS

J. J. McCormack et al., Dihydrofolate Reductase from Trypanosoma Equiperdum, II, Inhibition by 2,4-Diaminopyrimidines and Related Heterocycles, J. Med. Chem., 1969, vol. 12, pp. 662-668.
Morrison et al., Textbook "Organic Chemistry", Allyn and Bacon, Inc., 1973, Boston U.S., p. 733.
Bliss et al., Chemical Abstracts, vol. 102, entry 132066k (1985).
Bliss et al., Chemical Abstracts, vol. 108, entry 221657v (1988).

*Primary Examiner*—John M. Ford
*Attorney, Agent, or Firm*—Cushman, Darby & Cushman

[57] ABSTRACT 2,4-Diamino-5-phenylpyrimidines in the form of the free base or an acid addition salt thereof are provided having the structural formula (I):

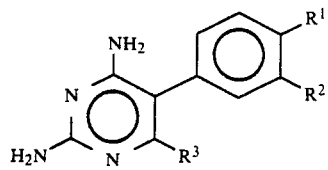

wherein $R^1$ is an alkoxy, aralkoxy or a mono-substituted or disubstituted amino group, $R^2$ is a nitro group, and $R^3$ is an alkyl group. The compounds act as antifolate agents and are useful for therapeutic treatment, for example as antitumour agents, antipsoriatic agents, antibacterial agents, antitrypanosomal agents and antimalarial agents. Pharmaceutical preparations comprising these compounds for administration to mammals, and methods for preparing the compounds, are disclosed. Particularly useful new compounds, especially for antitumour therapy, have the structural formula IA:

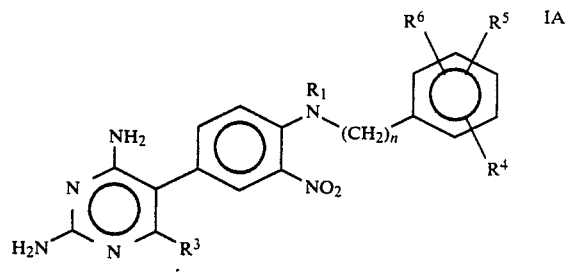

in which formula IA: n is 1-6; $R_1$ represents hydrogen or alkyl; $R^4$, $R^5$ and $R^6$, which may be identical or different, each represnt hydrogen, alkyl, alkoxy, halo, nitro, perfluoroalkyl, a group of formula —$CO_2R^a$ wherein $R^a$ represents hydrogen, alkyl or alkoxyalkyl, or a group of formula —$CONR^bR^c$ wherein $R^b$ and $R^c$ which may be identical or different each represent alkyl; and $R^3$ represents alkyl.

15 Claims, No Drawings

4,992,444

ANTIFOLATE AGENTS

TECHNICAL FIELD

This invention relates to antifolate agents and in particular to compounds useful in chemotherapy.

BACKGROUND ART

Antifolate agents, such as methotrexate, have been used as antitumor agents for many years and in 1954 metoprine (compound of formula I where $R^1$=Cl, $R^2$=Cl, $R^3$=Me) entered clinical trials.

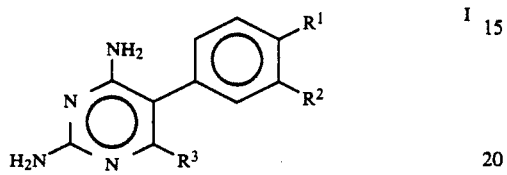

Although severe toxicity associated with this agent precluded further evaluation, the use of pyrimethamine (I, $R^1$=Cl $R^2$=H $R^3$=Et) has been explored and diaminopyrimidine compounds have also been developed which have inherent species selectivity as antibacterial and antimalarial agents.

Compounds have now been developed with inhibition of dihydrofolate reductase comparable to or greater than metoprine but which are relatively less toxic. These compounds are of interest as antiproliferative agents useful in the treatment of tumors, psoriasis, bacterial, malarial and trypanosomal infections.

Certain of such compounds are, however, disclosed as intermediates in an International Application (Published under No. WO84/04746) which relates to azido-substituted pyrimidine derivatives.

DISCLOSURE OF THE INVENTION

The present invention comprises, in a first aspect, a compound of formula I or an acid addition salt thereof for use in therapy, in which formula $R^1$ represents an alkoxy, aralkoxy or a mono- or disubstituted amino group, $R^2$ represents a nitro group, and $R^3$ represents an alkyl group.

The present invention further includes as novel substances within its scope at least the compounds of formula I per se and addition salts thereof where $R^1$ represents an aralkoxy group or a mono- or disubstituted amino group, $R^2$ represents a nitro group and $R^3$ an alkyl group.

In compounds of formula I in accordance with the invention, $R^1$ when representing an alkoxy group preferably contains 1-6 carbon atoms, the groups - OMe, OEt and OBu$^n$ being of particular interest, and when $R^1$ represents aralkoxy, benzyloxy is preferred. When present, amino groups are generally substituted by one or two alkyl or aralkyl groups in which the alkyl group or moiety preferably contains 1-6 carbon atoms, the following groupings representing $R^1$ being of particular interest: —NHMe, —NHEt, —NHBu$^n$, —NHCH$_2$CH$_2$Ph, —NHCH$_2$Ph, —NMeCH$_2$Ph, —N(CH$_2$Ph)$_2$, —NEtCH$_2$Ph, —NHCH(Me)Ph.

The alkyl group $R^3$, in preferred compounds, contains 1-6 carbon atoms, methyl and especially ethyl being of particular interest.

Many of the compounds in accordance with the invention as hereinbefore defined which are of particular interest, especially but not exclusively for use in therapy, may also be defined as being compounds of formula I, including acid addition salts thereof, characterised in that $R^1$ is a substituted amino group —NR$_1$R$_2$ where
R$_1$ is hydrogen or alkyl; and
R$_2$ is an aralkyl group having the structural formula IB

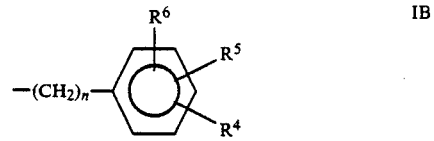

wherein $R^4$, $R^5$ and $R^6$ are independently:
hydrogen;
alkyl;
alkoxy;
halo;
nitro;
perfluoroalkyl;
—CO$_2$R$^a$ where R$^a$ is
hydrogen,
alkyl, or
alkoxyalkyl; or
—CONR$^b$R$^c$ where R$^b$ and R$^c$ are each alkyl, either identical or different or one of R$^b$ and R$^c$ is hydrogen and the other is alkyl.

Thus, in one particular more specific aspect the invention also provides a compound of formula IA or an acid addition salt thereof:

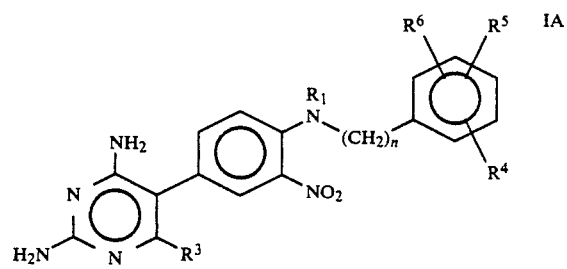

in which formula IA: n is 1-6; R$_1$ represents hydrogen or alkyl; $R^4$, $R^5$ and $R^6$, which may be identical or different, represent hydrogen, alkyl, alkoxy, halo, nitro, perfluoroalkyl, a group of formula —CO$_2$R$^a$ wherein R$^a$ represents hydrogen, alkyl or alkoxyalkyl, or a group of formula —CONR$^b$R$^c$ wherein R$^b$ and R$^c$ which may be identical or different each represent alkyl or one of R$^b$ and R$^c$ is hydrogen and the other is alkyl; and $R^3$ represents alkyl.

In preferred compounds of the invention in accordance with formula IA, alkyl groups, when present as such, or in other groups such as alkoxy groups, are generally $C_1$-$C_6$ alkyl, typically methyl or ethyl. $R^1$ typically represents hydrogen, methyl or ethyl and $R^3$, as already indicated, is a $C_1$-$C_6$ alkyl group, methyl and especially ethyl being preferred. In one particular range of preferred compounds at least one of R$_1$, $R^4$, $R^5$ and $R^6$ is other than hydrogen and/or at least one of $R^4$, $R^5$ and $R^6$ is other than hydrogen. When two of the radicals R , $R^5$ and $R^6$ are both hydrogen and the other radical is a substituent on the aromatic ring other than hydrogen, said other radical is carried at the 4-(para)

position in some preferred compounds. Halo substituents, when present, are generally fluorine or chlorine, and perfluoroalkyl is typically $C_1$-$C_4$ perfluoroalkyl, e.g. —$CF_3$. When the ring is substituted by —$CO_2R^a$, typically at the 4-position, $R^4$ and $R^5$ are usually both hydrogen. When $R^a$ represents hydrogen the compound generally exists in the form of a hydrate or other simple addition product. When $R^a$ represents alkyl, methyl and ethyl are generally preferred, and when $R^a$ represents alkoxyalkyl the group —$(CH_2)_x$—$OR^d$ in which $R^d$ represents $C_1$-$C_4$ alkyl and $x$ is 1 or 2, as in —$CH_2CH_2OEt$, is preferred.

The group —$CONR^bR^c$ is of particular interest especially when one of $R^b$ and $R^c$ represents hydrogen, the other representing alkyl, e.g. $C_1$-$C_4$ alkyl such as methyl or ethyl. Generally n is 1 in this case.

Compounds of formula IA of particular interest, wherein at least one of $R^4$, $R^5$ and $R^6$ is other than hydrogen, include the following:

| | | | | | |
|---|---|---|---|---|---|
| (a) $R^4 = 4\text{-}CO_2Me$ | $R^5 = H$ | $R^6 = H$ | $R^3 = Et$ | $R_1 = Me$ | $n = 1$ |
| (b) $R^4 = 4\text{-}CO_2(CH_2)_2OEt$ | $R^5 = H$ | $R^6 = H$ | $R^3 = Et$ | $R_1 = Me$ | $n = 1$ |
| (c) $R^4 = 4\text{-}OMe$ | $R^5 = H$ | $R^6 = H$ | $R^3 = Et$ | $R_1 = Me$ | $n = 1$ |
| (d) $R^4 = 4\text{-}OMe$ | $R^5 = H$ | $R^6 = H$ | $R^3 = Et$ | $R_1 = H$ | $n = 1$ |
| (e) $R^4 = 4\text{-}CONHMe$ | $R^5 = H$ | $R^6 = H$ | $R^3 = Et$ | $R_1 = Me$ | $n = 1$ |
| (f) $R^4 = 4\text{-}CO_2H$ | $R^5 = H$ | $R^6 = H$ | $R^3 = Et$ | $R_1 = Me$ | $n = 1$ |
| (g) $R^4 = 4\text{-}Cl$ | $R^5 = H$ | $R^6 = H$ | $R^3 = Et$ | $R_1 = H$ | $n = 1$ |
| (h) $R^4 = 4\text{-}Me$ | $R^5 = H$ | $R^6 = H$ | $R^3 = Et$ | $R_1 = H$ | $n = 1$ |
| (i) $R^4 = 4\text{-}F$ | $R^5 = H$ | $R^6 = H$ | $R^3 = Et$ | $R_1 = H$ | $n = 1$ |
| (j) $R^4 = 4\text{-}OMe$ | $R^5 = 3\text{-}OMe$ | $R^6 = H$ | $R^3 = Et$ | $R_1 = H$ | $n = 1$ |
| (k) $R^4 = 2\text{-}Cl$ | $R^5 = H$ | $R^6 = H$ | $R^3 = Et$ | $R_1 = H$ | $n = 1$ |
| (l) $R^4 = 4\text{-}Cl$ | $R^5 = 3Cl$ | $R^6 = H$ | $R^3 = Et$ | $R_1 = H$ | $n = 1$ |
| (m) $R^4 = 2\text{-}OMe$ | $R^5 = 4\text{-}OMe$ | $R^6 = 6\text{-}OMe$ | $R^3 = Et$ | $R_1 = H$ | $n = 1$ |
| (n) $R^4 = 4\text{-}CF_3$ | $R^5 = H$ | $R^6 = H$ | $R^3 = Et$ | $R_1 = H$ | $n = 1$ |
| (o) $R^4 = 4\text{-}F$ | $R^5 = H$ | $R^6 = H$ | $R^3 = Et$ | $R_1 = Me$ | $n = 1$ |

Compound (f) generally exists in the form of a hydrate. Compounds (e), (l) and (n) at least are of particular interest, especially Compound (l), for the treatment of tumors.

In general compounds in accordance with the present invention are preparable by replacement of chlorine in a nitropyrimethamine IC:

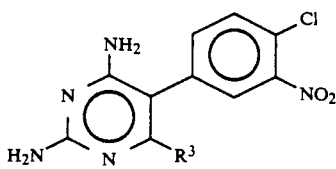

by the residue of the required group $R^1$.

When $R^1$ represents alkoxy (or aralkoxy), the required compounds may be prepared as described in the International Application published under No. WO(84/04746, which discloses their use as intermediates. When, however, $R^1$ represents a mono- or disubstituted amino group, —$NR_1R_2$, wherein $R_1$ and $R_2$ represent hydrogen or substituents such as an alkyl or aralkyl group as hereinbefore specified, the compounds may be prepared in accordance with a further aspect of the present invention by treating a nitropyrimethamine, i.e. a compound of formula IC, with a compound of formula $R_1R_2NH$.

The reaction may take place in some cases in the absence of additional solvent but with application of heat, the reagent $R_1R_2NH$ acting as both reactant and solvent. In other cases, particularly in preparing compounds of formula IA, typically the reaction is conducted in a polar solvent, for example an alcohol such as methanol, ethanol or 2-ethoxyethanol, and heat is usually applied.

In accordance with a further aspect of the present invention a compound of formula IA is produced by treating a compound of formula IC with a compound of formula ID:

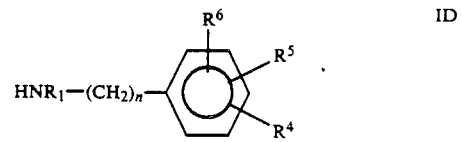

wherein n, $R^1$, $R_4$, $R^5$ and $R^6$ are as hereinbefore defined.

In some cases, compound ID being a benzylamine may itself first be prepared by reduction of the corresponding benzylamide, e.g. by treatment with a hydride such as lithium aluminium hydride in a non-aqueous solvent. The benzylamide may be prepared by reacting a benzoyl chloride with an alkylamine.

Acid addition salts of compounds of formula (I) and of formula (IA) in accordance with the invention are preferably pharmaceutically acceptable although other acid addition salts are within the scope of the invention. Suitable salts are those derived from, for example, the following acids: hydrochloric, hydrobromic, sulphuric, nitric, isethionic, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic. The preferred salts in terms of pharmaceutical acceptability are the ethanesulphonic acid salts.

Such salts may be prepared from the free-base by treatment with the acid suitably in a polar solvent such as water and if necessary with the application of heat.

The compounds of the invention have been found to inhibit dihydrofolate reductase (DHFR) in mammals and other biological systems and to have antitumor activity. Insofar as they are lipophilic they can be of particular interest for the treatment of tumors and malignancies, such as in the central nervous system for instance, inaccessible to polar agents. They are also of interest in relation to antipsoriatic, antibacterial and anti-malarial activity. Antitumor activity is evidenced for example by reduction of tumor cell number in mammals bearing ascitic tumors and their consequent increase in survival as compared to a control group which is untreated. Antitumor activity is further evidenced by measurable reduction in the size of solid tumors following treatment with the compounds of this invention compared to the tumors of untreated control animals. The murine tumor lines against which the compounds in accordance with the invention of formula (I) are envisaged active include, but are not limited to, lymphocytic leukaemia P388, lymphocytic leukaemia L1210, melanotic melanoma B16, Colon 38, TLX5 lymphoma, W3129 myeloma, Walker 256 and M5 reticulum cell sarcoma.

As has been described above, the compounds of the present invention are of interest for the treatment of tumors, psoriasis, malarial or trypanosomal and bacterial infection; the invention thus further provides a method for the treatment of a patient with a tumor or a psoriatic, trypanosomal or bacterial disease. For this purpose, an effective non-toxic amount of the compound of formula (I), or an acid addition salt thereof, may be suitably administered, orally, parenterally (including subcutaneously, intramuscularly and intravenously), or topically. The administration will generally be carried out repetitively at intervals, for example once or several times a day.

The amount of compounds of formula (I), as hereinbefore defined in accordance with the invention, which is required in order to be effective as an antitumor, anti-psoriatic, antibacterial or antitrypanosomal agent for treating mammals will, of course, vary and is ultimately at the discretion of the medical or veterinary practitioner treating the mammal in each particular case. The factors to be considered by such a practitioner, e.g. a physician, include the route of administration and pharmaceutical formulation; the mammal's body weight, surface area, age and general condition; and the particular salt to be administered. However, a suitable effective antitumor dose is in the range of about 1.0 to about 75 mg/kg bodyweight, preferably in the range of about 5 to 40 mg/kg with most suitable doses being for example in the range 10 to 30 mg/kg. In daily treatment for example, the total daily dose may be given as a single dose, multiple doses, e.g. two to six times per day, or by intravenous infusion for any selected duration. For example, for a 75 kg mammal, the dose range would be about 75 to 500 mg per day, and a typical dose would commonly be about 100 mg per day. If discrete multiple doses are indicated, treatment might typically be 50 mg of a compound of formula (I), as hereinbefore defined, given 4 times per day in the form of a tablet, capsule, liquid (e.g. syrup) or injection.

The activity of these compounds of formula (I) usually resides in the free base and thus the nature of the acid participating in the acid addition salts may be of minor importance. However, when used in medicine, the salts of these compounds of formula (I) will normally be pharmacologically and pharmaceutically acceptable, but non-pharmaceutically and non-pharmacologically acceptable salts may conveniently be used to prepare the free active compound or pharmaceutically acceptable salts thereof and are not excluded from the scope of this invention.

While it is possible for the active compound of this invention [defined herein as a compound of formula (I) with substituents as previously specified] to be administered alone as the raw chemical, it is preferable to present the active compound as a pharmaceutical formulation. Formulations of the present invention, for medical use, comprise the active compound together with one or more pharmaceutically acceptable carriers thereof and, optionally, any other therapeutic ingredients. The carrier(s) must be pharmaceutically acceptable in the sense of being compatible with the other ingredients of the formulation and not deleterious to the recipient thereof.

The present invention therefore further provides a pharmaceutical formulation comprising a compound of formula (I) with substituents as hereinbefore specified (in the form of the free base or a pharmaceutically acceptable acid addition salt) together with a pharmaceutically acceptable carrier thereof.

The formulations include those suitable for oral, rectal, topical or parenteral (including subcutaneous, intramuscular and intravenous) administration.

The formulations may conveniently be presented in unit dosage form and may be prepared by any of the methods well known in the art of pharmacy. All methods include generally the step of bringing the active compound into association with a carrier which constitutes one or more accessory ingredients. Usually, the formulations are prepared by uniformly and intimately bringing the active compound into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallization of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parental administration conveniently comprise a sterile aqueous preparation of the active compound which is preferably isotonic with the blood of the recipient.

In addition to the aforementioned ingredients, formulations of this invention, for example ointments, creams and the like, may include one or more accessory ingredient(s) selected from diluents, buffers, flavouring agents, binders, surface active agents, thickeners, lubricants, preservatives (including antioxidants) and the like.

From another aspect, the invention thus also comprises use of a compound of formula I with substituents as hereinbefore specified, or an acid addition salt thereof, for the manufacture of a medical preparation for the treatment of tumors, psoriasis, bacterial, malarial and/or trypanosomal infections in mammals.

Overall, the invention comprises each and any novel feature or combination of features disclosed herein, but different aspects of the invention principally but not exclusively comprise broadly the following:

(i) Compounds of formula (I) with substituents as hereinbefore defined for therapy or for use in medicine and in the manufacture of medical preparations, for example as antitumor agents, antipsoriatic agents, antimalarial agents, anti-bacterial agents, and antitrypanosomal agents;

(ii) Novel compounds of formula (I) or (Ia) as defined herein;

(iii) Processes for the preparation of novel compounds of formula (I) or (Ia) as defined herein, including any novel intermediate compounds produced in carrying out such processes;

(iv) A pharmaceutical formulation comprising a compound of formula (I) or (Ia) as defined herein together with a pharmaceutically acceptable carrier therein;

(v) Processes for the preparation of a pharmaceutical formulation as defined in (iv) above by methods described herein.

DESCRIPTION OF EXAMPLES OF PREFERRED EMBODIMENTS

The following examples and descriptions of stages in synthetic routes of preparation of preferred compounds illustrate the present invention but should not be construed in any way as a limitation thereof.

EXAMPLE 1

2,4-Diamino-5-(4-methylamino-3-nitrophenyl)-6-ethylpyrimidine (Compound 1)

A suspension of 2,4-Diamino-5-(4-chloro-3-nitro phenyl)-6-ethylpyrimidine (nitropyrimethamine) (10 g) in aqueous methylamine solution (40%; 200 ml) was refluxed for 48 hours with the further addition of methylamine solution (100 ml) after 24 hours and 36 hours. An orange colour slowly developed and the consumption of starting material was monitored by t.l.c. After cooling and dilution with water, the crystalline product was collected and recrystallized from aqueous DMF to yield orange prisms of 2,4-Diamino-5-(4-methylamino-3-nitrophenyl)-6-ethylpyrimidine (9.0 g. 92%), m.p. 262°–265° C (Elemental analysis: C, 53.9; H, 5.9; N, 29.3%; calculated: C, 54.2; H, 5.6; N, 29.2%).

EXAMPLE 2

2,4-Diamino-5-(4-ethylamino-3-nitrophenyl)-6-ethylpyrimidine (2)

A suspension of nitropyrimethamine (10 g) in aqueous ethylamine solution (70%; 200 ml) was refluxed for 48 hours with the further addition of ethylamine solution (100 ml) after 24 hours and 36 hours. An orange colour slowly developed and the consumption of starting material was monitored by t.l.c. After cooling and dilution with water, the crystalline product was collected and recrystallized from aqueous DMF to yield orange prisms of 2,4-diamino-5-(4-ethylamino-3-nitrophenyl)-6-ethylpyrimidine (9.0 g, 87%), m.p. 275°–276° C (Elemental analysis: C, 55.6; H, 5.9; N, 28.0%; calculated: C, 55.6; H, 6.0; N, 27.8%).

EXAMPLE 3

2,4-Diamino-5-(4-dimethylamino-3-nitrophenyl)-6-ethylpyrimidine (3)

To a solution of nitropyrimethamine (2 g) in DMF (10 ml) at 94° C (bath temperature) was added 2-aminoethanol (0.84 g) dropwise over 5 minutes, and the mixture was stirred overnight at the same temperature. The deep red mixture was cooled, diluted with water (50 ml) and allowed to stand at 4° C overnight, when a red crystal mass deposited and was collected and recrystallized from aqueous DMF to give orange prisms of 2,4-diamino-5-(4-dimethylamino-3-nitrophenyl)-6-ethylpyrimidine (1.8 g, 87%), m.p. 256°–258° C. (Elemental analysis: C, 55.6; H, 5.9; N, 27.8%; calculated C, 55.6; H, 5.9; N, 27.8%).

EXAMPLE 4

2,4-Diamino-5-(4-dimethylamino-3-nitrophenyl)-6-ethylpyrimidine (3)

A suspension of nitropyrimethamine (10 g) in aqueous dimethylamine solution (40%; 200 ml) was refluxed for 48 hours with the further addition of dimethylamine solution (100 ml) after 24 hours and 36 hours. An orange colour slowly developed and the consumption of starting material was monitored by t.l.c. After cooling and dilution with water, the crystalline product was collected and recrystallized from aqueous DMF to yield orange prisms of 2,4-diamino-5-(4-dimethylamino-3-nitrophenyl)-6-ethylpyrimidine (7.0 g, 68%). m.p. 256°–257° C (Elemental analysis: C, 55.6; H, 5.9; N, 27.4%; calculated: C, 55.6; H, 5.9; N, 27.8%).

EXAMPLE 5

2,4-Diamino-5-(4-n-butylamino-3-nitrophenyl)-6-ethylpyrimidine (4)

A suspension of the nitropyrimethamine (10 g) in n-butylamine (30 ml) was refluxed for 4 hours. The deep red liquor was cooled, diluted with water and stood for 12 hours, whereupon red crystals deposited and were collected. Recrystallization from aqueous 2-ethoxyethanol gave crimson plates of the 2,4-diamino-5-(4-n-butylamino-3-nitrophenyl)-6-ethylpyrimidine (11.0 g. 95%), m.p. 252°–254° C (Elemental analysis: C, 58.2; H, 6.8; N, 25.5%; calculated: C, 58.2; H, 6.7; N, 25.5%).

EXAMPLE 6

2,4-Diamino-5-(4-benzylamino-3-nitrophenyl)-6-ethylpyrimidine (5)

A solution of nitropyrimethamine (2 g) in benzylamine (20 ml) was boiled for 4 hours, cooled and poured into ether (50 ml). The precipitate was washed with ether, and then water and subsequently recrystallized from 2-ethoxyethanol to give red microprisms of 2,4-diamino-5-(4-benzylamino-3-nitrophenyl)-6-ethylpyrimidine (1.8 g, 73%), m.p. 253°–255° C (Elemental analysis: C, 63.0; H, 5.8; N, 23.3%; calculated: C, 62.6; H, 5.5; N, 23.1%).

EXAMPLE 7

2,4-Diamino-6-ethyl-5-(4-N-methylbenzylamino-3-nitrophenyl)pyrimidine (6)

A solution of nitropyrimethamine (2 g) in N-methylbenzylamine (20 ml) was boiled for 4 hours, cooled and poured into ether (50 ml). The precipitate was washed with ether, and then water and subsequently recrystallized from aqueous ethoxyethanol to give red microprisms of 2,4-diamino-6-ethyl-5-(4-N-methylbenzylamino-3-nitrophenyl)-pyrimidine (2.3 g. 91%), m.p. 210°–211° C (Elemental analysis: C, 63.5; H, 6.1; N, 22.3%; calculated: C, 63.5; H, 5.8; N, 22.2%).

EXAMPLE 8

2,4-Diamino-6-ethyl-5-(4-N-ethylbenzylamino-3-nitrophenyl)pyrimidine (7)

A solution of nitropyrimethamine (2 g) in N-ethylbenzylamine (20 ml) was boiled for 4 hours, cooled and poured into ether (50 ml). The precipitate was washed with ether, and then water and subsequently recrystallized from aqueous ethoxyethanol to give red microprisms of 2,4-diamino-6-ethyl-5-(4-N-ethylbenzylamino-3-nitrophenyl)pyrimidine (2.3 g, 86%), m.p. 214°–216° C (Elemental analysis: C, 64.2; H, 6.2; N, 21.1%; calculated: C, 64.3; H, 6.1; N, 21.4%).

EXAMPLE 9

2,4-Diamino-5-(4-dibenzylamino-3-nitrophenyl)-6-ethylpyrimidine (8)

A solution of nitropyrimethamine (2 g) in dibenzylamine (20 ml) was boiled for 4 hours, cooled and poured into ether (50 ml). The precipitate was washed with ether, and then water and subsequently recrystallized from aqueous ethoxyethanol to give red microprisms of 2,4-diamino-5-(4-dibenzylamino-3-nitrophenyl)-6-ethylpyrimidine (1.5 g, 49%), m.p. 197°–199° C (Elemental analysis: C, 68.6; H, 5.6; N, 18.3%; calculated: C, 68.7; H, 5.7; N, 18.5%).

EXAMPLE 10

2,4-Diamino-6-ethyl-5-(4-(+)-α-methylbenzylamino-3-nitrophenyl)pyrimidine (9)

A solution of nitropyrimethamine (2 g) in (±)α-methylbenzylamine (20 ml) was boiled for 4 hours, cooled and poured into ether (50 ml). The precipitate was washed with ether, and then water and subsequently recrystallized from ethyl acetate to give red microprisms of 2,4-diamino-6-ethyl-5-(4-(±)-α-methylbenzylamino-3-nitrophenyl)-pyrimidine (2.2 g, 85%), m.p. 208°–210° C (Elemental analysis: C, 63.5; H, 5.9; N, 22.2%; calculated: C, 63.5; H, 5.8; N, 22.2%).

EXAMPLE 11

2,4-Diamino-6-ethyl-5-(3-nitro-4-phenethylaminophenyl)-pyrimidine (10)

A mixture of nitropyrimethamine (5 g) and phenethylamine (20 ml) was boiled for 4 hours, cooled and poured into ether (100 ml). The precipitate was washed with ether and then water, and subsequently recrystallized from aqueous ethoxyethanol to furnish red needles of 2,4-diamino-6-ethyl-5-(3-nitro-4-phenethylaminophenyl)-pyrimidine (4.5 g, 70%), m.p. 222°–225° C (sinters) (Elemental analysis: C, 63.7; H, 6.2; N, 22.4%; calculated: C, 63.5; H, 5.8; N, 22.2%).

EXAMPLE 12

2,4-Diamino-5-(4-N-methylbenzylamino-3-nitrophenyl)-6-methylpyrimidine (11)

2,4-Diamino-5-(4-chloro-3-nitrophenyl)-6-methylpyrimidine (0.01 mol. equiv.) was heated with N-methylbenzylamine (15 ml) at 150° C for 2 hours. The mixture was poured into ether (50 ml) and the solid product collected, washed with ether, and crystallized from aqueous 2-ethoxyethanol.

EXAMPLE 13

2,4-Diamino-5-(4-N-methylbenzylamino-3-nitrophenyl)-6-methylpyrimidine ethanesulphonate salt (12)

The pyrimidine free-base from above (0.4 g) was suspended in water (5 ml) and ethanesulphonic acid (0.13 g; 1.1 mol. equiv.) was added. The mixture was gently boiled with the further addition of water until dissolution occured. The solution was allowed to cool and the red solid (0.5 g) was collected and recrystallized from water to furnsh orange microcrystals (0.4 g; 77%), m.p. 253°–254° C (Found: M+, 364). $C_{19}H_{20}N_6O_2$ (free base) requires M.W. 364; Found: C, 53.04; H, 5.52; N, 17.65%. $C_{21}H_{26}N_6SO_5$ requires C, 53.16; H, 5.49; N, 17.72%.

EXAMPLES 14 AND 14a 2,4-Diamino-5-(4-N-methylbenzylamino-3-nitrophenyl)-6-ethylpyrimidine (Compound 13) and 2,4-Diamino-5-(4-N-methylbenzylamino-3-nitrophenyl)-6-ethylpyrimidine ethanesulphonate salt (14)

The pyrimidine free-base (Methobenzaprim, MBP) was prepared by the same method as in Example 12 but using 2,4-Diamino-5-(4-chloro-3-nitrophenyl)-6-ethylpyrimidine (nitropyrimethamine). On crystallization from aqueous 2-ethoxyethanol a 91% yield was obtained, m.p. 210°–211° C (Found: C, 63.5; H, 6.1; N, 22.3%. $C_{20}H_{22}N_6O_2$ requires C, 63.5; H, 5.8; H, 22.2%). To obtain the ethanesulphonate salt this compound (1.0 g) was suspended in water (5ml) and ethanesulphonic acid (1.1 mol. equiv.) was added. The mixture was gently boiled with the further addition of water until dissolution occured. The solution was allowed to cool and the red solid was collected and recrystallized from water to furnish orange microcrystals (1.1 g; 85%), m.p. 242°–243° C (Found: M+, 378). $C_{20}H_{22}N_6O_2$ (free base) requires M.W. 378.

EXAMPLE 15

2,4-Diamino-6-ethyl-5-{4-[N-(4-methoxycarbonylbenzyl)-N-methylamino]-3-nitrophenyl}pyrimidine (15)

Methyl 4-(methylaminomethyl)benzoate (1.06 g. 6 mmol), nitropyrimethamine (1) (860 mg, 3 mmol), triethylamine (0.8 ml, 9 mmol) and 2-ethoxyethanol (10 ml) were boiled together under reflux for 72 hours. The 2-ethoxyethanol was evaporated under reduced pressure. The dark red/brown viscous liquid was subjected to column chromatography (silica; chloroform 95%; methanol 5%) which, after removal of the solvent under reduced pressure, yielded a yellow oil. Trituration in petroleum ether furnished an orange solid (190 mg). NMR and MS analysis indicated the presence of two compounds. This mixture was boiled under reflux in methanol (30 ml) with concentrated sulphuric acid (0.5 ml) for 6 hours. The methanol was evaporated under reduced pressure and the resulting solid was taken up in aqueous 10% potassium carbonate and extracted with ethyl acetate (3 x 50 ml). The ethyl acetate layer was dried ($Na_2SO_4$), filtered and the solvent was evaporated under reduced pressure to furnish an orange powder (160 mg. 6%). m.p. 198°–200° C (Found: C, 60.34; H, 5.77; N, 18.90%. $C_{22}H_{24}N_6O_4$ requires C, 60.55; H, 5.50; N, 19.27%.

EXAMPLE 16

2,4-Diamino-6-ethyl-5-(4-{N-[4-(2-ethoxyethoxy)carbonylbenzyl]-N-methylamino}-3-nitrophenylpyrimidine (16)

2-Ethoxyethyl 4-(methylaminomethyl)benzoate (10.7 g), nitropyrimethamine (3.5 g, 12 mmol) and 2-ethoxyethanol (10 ml) were boiled under reflux for 20 hours before the solvent was evaporated under reduced pressure. The dark red oil was subjected to column chromatography (silica; chloroform 90%; methanol 10%) and the solvent was evaporated under reduced pressure. Trituration in diethyl ether furnished the 2-ethoxyethyl ester as a yellow powder (180 mg). m.p. 114°–116° C (Found: C, 60.55; H, 6.08; N,17.17%. $C_{25}H_{30}N_6O_5$ requires C, 60.73; H, 6.07; N, 17.00%).

EXAMPLE 17

2,4-Diamino-6-ethyl-5-{4-[N-(4-methoxybenzyl)-N-methylamino]-3-nitrophenyl}pyrimidine (17)

N-Methyl-4-methoxybenzylamine (4.07g, 27 mmol), nitropyrimethamine (2.0 g, 6.8 mmol) and 2-ethoxyethanol (20 ml) were boiled under reflux for 12 hours. After the mixture was poured into diethyl ether and allowed to cool, filtration furnished an orange powder. This was washed with water, dried and crystallized from aqueous 2-ethoxyethanol to yield the product as an orange powder (680 mg, 24.5%). m.p. 201°–203° C (Found: C, 61.61; H, 5,97; N, 20.44%. $C_{21}H_{24}N_6O_3$ requires C, 61.76; H, 5.88; N, 20.59%).

EXAMPLE 18

2,4-Diamino-6-ethyl-5-{4-[N-(4-methoxybenzyl)amino]-3-nitrophenyl}pyrimidine (18)

4-Methoxybenzylamine (3.6g, 27.2 mmol), nitropyrimethamine (2.0 g, 6.8 mmol) and 2-ethoxyethanol (15 ml) were heated together under reflux for 12 hours. The solution was poured into diethyl ether, filtered and washed with water. The resulting orange powder crystallized from aqueous 2-ethoxyethanol to yield the red crystalline compound (930 mg, 35%). m.p. 241°–242° C (Found: C, 60.76; H, 5,74; N, 21.59%. $C_{20}H_{22}N_6O_3$ requires C, 60.91; H, 5.58; N, 21.32%).

EXAMPLE 19

2,4-Diamino-6-ethyl-5-(4-{N-[4-(N-methylcarbamoyl)benzyl]-N-methylamino}-3-nitrophenyl)pyrimidine (19)

N-Methyl-4-(methylaminomethyl)benzamide (2.56 g, 14.4 mmol), nitropyrimethamine (2.1 g, 7.2 mmol) and 2-ethoxyethanol (25 ml) were boiled under reflux for 6 hours. The reaction mixture was then poured into water and allowed to cool in the refrigerator. The precipitate was filtered and washed to furnish a pale orange powder (800 mg, 26%). m.p. 235°–237° C (Found: C, 60.22; H, 5.73; N, 21.99. $C_{22}H_{25}N_7O_3$ requires C, 60.69; H, 5.75; N, 22.53%).

EXAMPLE 20

2,4-Diamino-6-ethyl-5-{4-[N-(4-carboxybenzyl)-N-methylamino]-3-nitrophenyl}pyrimidine monohydrate (20)

The methyl ester (1) (0.92 g, 2.11 mmol) and sodium hydroxide (500 mg, 12.5 mmol) in methanol (25 ml) were boiled under reflux for 16 hours. The mixture was allowed to cool to room temperature before concentrated hydrochloric acid was added dropwise to pH 6.0. After the precipitate formed was filtered and washed with methanol producing an orange powder (720 mg), it was suspended in water and boiled in a solution of aqueous ethanesulphonic acid (0.21 g, 1.88 mmol). On cooling, a yellow precipitate was formed which was filtered and crystallized from water to yield the product as a yellow powder (410 mg, 44%). m.p. 244°–246° C (Found: C, 56.88; H, 5.43; N, 18.90%. $C_{21}H_{24}N_6O_5$ requires C, 57.27, H, 5.45; N, 19.10%).

EXAMPLES 21–28

The following compounds (21–28) were prepared by Method A, B or C:

| | | | | | | |
|---|---|---|---|---|---|---|
| (21)IA: $R^4$ = 2-Cl | $R^5$ = H | $R^6$ = H | $R^3$ = Et | $R_1$ = H | n = 1 |
| (22)IA: $R^4$ = 4-Cl | $R^5$ = H | $R^6$ = H | $R^3$ = Et | $R_1$ = H | n = 1 |
| (23)IA: $R^4$ = 4-Cl | $R^5$ = 3-Cl | $R^6$ = H | $R^3$ = Et | $R_1$ = H | n = 1 |
| (24)IA: $R^4$ = 4-F | $R^5$ = H | $R^6$ = H | $R^3$ = Et | $R_1$ = H | n = 1 |
| (25)IA: $R^4$ = 4-Me | $R^5$ = H | $R^6$ = H | $R^3$ = Et | $R_1$ = H | n = 1 |
| (26)IA: $R^4$ = 4-OMe | $R^5$ = 3-OMe | $R^6$ = H | $R^3$ = Et | $R_1$ = H | n = 1 |
| (27)IA: $R^4$ = 4-OMe | $R^5$ = 2-OMe | $R^6$ = 6-OMe | $R^3$ = Et | $R_1$ = H | n = 1 |
| (28)IA: $R^4$ = 4-CF$_3$ | $R^5$ = H | $R^6$ = H | $R^3$ = Et | $R_1$ = H | n = 1 |

Method A 2,4-Diamino-5-(4-chloro-3-nitrophenyl)-6-ethylpyrimidine ('nitropyrimethamine'; 1) (0.01 mol. equiv) was heated with the appropriate benzylamine (15 ml) at 150° C. for 2 hours. The mixture was poured into ether (50 ml) and the solid product was collected, washed with ether, and crystallized from aqueous 2-ethoxyethanol.

Method B

Nitropyrimethamine (0.01 mol. equiv), 2-chlorobenzylamine (10 ml) and 2-ethoxyethanol (10 ml) were boiled (10 h). The red solution was diluted with ether (50 ml) and the orange product, 2,4-diamino-5-[4-(2-chlorobenzylamino)-3-nitrophenyl]-6-ethylpyrimidine (21) was collected (55%). The product had m.p. 243°–244° C (Found: M+, 398. $C_{19}H_{19}ClN_6O_2$ requires M.W. 398).

Method C

Nitropyrimethamine (0.01 mol. equiv.), the substituted benzylamine hydrochloride salt (0.04 mol. equiv), triethylamine (0.04 mol. equiv) and 2-ethoxyethanol (30 ml) were refluxed for 10 h. The mixture was poured into ether (50 ml) and the product collected and washed with ether, followed by water. Crystallization from aqueous 2-ethoxyethanol afforded the diaminopyrimidine.

The following products were prepared by Method A: 2,4-Diamino-5-[4-(4-chlorobenzylamino)-3-nitrophenyl]-6-ethylpyrimidine (22), from 4-chlorobenzylamine, m.p. 247°–248° C (75% yield) (Found: M+, 398 (400). $C_{19}H_{19}ClN_6O_2$ requires M.W. 398 (400); Found:

C, 56.1; H, 4.8, N, 21.1%. $C_{19}H_{19}ClN_6O_2$ requires C, 57.2; H, 4.7; N, 21.1%.

2,4-Diamino-5-[4-(4-methylbenzylamino)-3-nitrophenyl]-6-ethylpyrimidine (25), from 4-methylbenzylamine, (85% yield) m.p. 237°-238° C (Found: M+, 378. $C_{20}H_{22}N_6O_2$ requires M.W. 378); Found: C, 63.25; H, 5.9; N, 22.55%. $C_{20}H_{22}N_6O_2$ requires C, 63.4; H, 5.8; N, 22.2%.

2,4-Diamino-5-[4-(4-fluorobenzylamino)-3-nitrophenyl]-6-ethylpyrimidine (24), from 4-fluorobenzylamine, m.p. 250°-251° C (60% yield) (Found: M+, 382. $C_{19}H_{19}FN_6O_2$ requires M.W. 382); Found: C, 59.2; H, 5.0; N, 21.3%. $C_{19}H_{19}FN_6O_2$ requires C, 59.7; H, 5.0; N, 22.0%.

2,4-Diamino-5-[4-(3,4-dimethoxybenzylamino)-3-nitrophenyl]-6-ethylpyrimidine (26), from 3,4-dimethoxy-benzylamine, m.p. 232°-233° C (95% yield) (Found: M+, 424. $C_{21}H_{22}N_6O_4$ requires M.W. 424). Found: C, 59,6; H, 5.85, N, 18.5%. $C_{21}H_{22}N_6O_2$ requires C, 58.4; H, 5.7; N, 19.8%.

The following compound (28) was prepared by Method B:

2,4-diamino-5-[3-nitro-4-(4-trifluoromethylbenzylamino)phenyl]-6-ethylpyrimidine (28), (40% yield) m.p. 253°-254° C (Found: M+, 432, $C_{20}H_{19}F_3N_6O_2$ requires M.W. 432);

The following compounds were prepared by Method C:

2,4-Diamino-5-[4-(3,4-dichlorobenzylamino)-3-nitrophenyl]-6-ethylpyrimidine (23), from 3,4-dichlorobenzylamine hydrochloride, yield 65%, m.p. 244°-245° C (Found: M+, 433. $C_{19}H_{18}Cl_2N_6O_2$ requires M.W. 433)

2,4-Diamino-5-[4-(2,4,6-trimethoxybenzylamino)-3-nitrophenyl]-6-ethylpyrimidine (27), from 2,4,6-trimethoxybenzylamine hydrochloride, (Found: M+, 454. $C_{22}H_{26}N_6O_5$ requires M.W. 454).

EXAMPLE 29

2,4-Diamino-6-ethyl-5-(4-{N-[4-fluorobenzyl]-N-methylamino}-3-nitrophenyl)pyrimidine (29)

This compound was prepared from 4-Fluoro-N-methylbenzylamine which in turn was prepared from 4-Fluoro-N-methylbenzamide. Practical details are as follows: 4-Fluorobenzoyl chloride (25g) was added dropwise to a stirred aqueous solution of methylamine (40% w/v; 250 ml) at 0° C over 30 min. The mixture was stirred for 12 h at room temperature, concentrated to half volume and the resulting crystalline precipitate was collected and recrystallized from water to furnish the N-methylbenzamide as colourless needles, (24.1 g; 89.1%), m.p. 131°-132° C.

To a stirred solution of lithium aluminium hydride (10 g) in dry tetrahydrofuran (250 ml) was added a solution of the 4-fluoro-N-methylbenzamide (21.6 g) in dry tetrahydrofuran (150 ml) dropwise over 1 h at room temperature. When effervescence had subsided the mixture was gently heated under reflux for 24 h when Tlc analysis indicated the absence of starting materials. After cooling the mixture, water (10 ml) was added cautiously over 2 h, followed by 2M sodium hydroxide solution (30 ml), and finally water (10 ml), whereupon the suspension was stirred for a further 30 min and solids were removed by filtration through Celite. The filtrate was evaporated to dryness under vacuo and the residue was redissolved in ethyl acetate (200ml), and dried over sodium sulphate. Removal of the ethyl acetate furnished the N-methylbenzylamine product in the form of a pale yellow oil (14.3g; 72.6%) which was used without further purification.

Nitropyrimethamine (2 g) was added to a solution of the above 4-Fluoro-N-methylbenzylamine (5 g) in 2-ethoxyethanol (5 ml) and the mixture was stirred at 160° C (oilbath temperature) for 12 h, when Tlc analysis confirmed product formation. The orange mixture was cooled, poured into diethyl ether (100 ml) and stood at 4° C for 12 h, when the orange solid which precipitated was collected and washed with ether (3×100 ml), followed by water (2×100 ml) to afford a yellow powder (1.5 g; 55.6%).

The fluorobenzylpyrimidine free base obtained was converted to the corresponding ethanesulphonate salt as follows: ethanesulphonic acid (0.24 g) was added dropwise to a suspension of the free base (0.8 g) in water (10 ml) and the mixture was heated to boiling whereupon dissolution occurred. The yellow solid which deposited on cooling was collected and recrystallized twice from water to give the ethanesulphonate salt as an orange powder (0.46 g; 45%). (Found: C, 52.07; H, 5.52; F, 3.90; N, 17.21%. $C_{22}H_{27}FN_6O_5S$ requires C, 52.17; H, 5.34; F, 3.75; N, 16.60%

Compounds of the preceding Examples were subjected to tests for DHFR inhibition, antitumor activity against the P388 leukaemia and M5076 reticulum cell sarcoma in mice, and for cytotoxicity against L1210 cells in vitro, the results of some of which are shown in Tables I-VII. The following methods and materials were used;

A. Compound dissolution Stock inhibitor solutions were prepared by dissolving the appropriate compound in water, 0.1 M-hydrochloric acid or ethanol to give a final concentration of $1 \times 10^{-3}$M. Where difficulties in dissolving the compound were encountered the mixture was warmed in a water bath at 40° C before dilution to the requisite volume. All solutions were prepared on the day previous to the experiment and stored in the dark at 4° C prior to use.

The stock solutions were diluted, as necessary, immediately before use to produce the required inhibitor concentration. Following further dilution in the final reaction mixture, the highest solvent concentrations were $5 \times 10^{-3}$ M and $1.1 \times 10^2$ M for hydrochloric acid and ethanol respectively. No effect on DHFR activity was observed at these solvent concentrations.

B. The DHFR Assays

B.1 Preparation of partially purified DHFR

Partially purified enzyme was prepared by the method of J. R. Bertino and G. A. Fischer (Meth. Med. Res., 1964, 10, 297), as follows: Two male Wister rats were killed and the livers were removed rapidly and washed with water to remove blood. All further manipulations were performed at 4° C: the livers (30.7 g) were transferred to a Waring blender to which approximately 8 volumes of water was added (final volume c.a. 300 ml), whereupon the mixture was homogenised for 2 minutes for periods of 30s, allowing 30s between each run to minimise heating. Liver homogenate was centrifuged at approximately 20,000 g for 20 minutes and the pellet was discarded. The supernatant liquid was adjusted to pH 5.1 with dilute acetic acid (1.0 M initially and 0.1 M finally) and after centrifugation at 27,000 g for a further 20 minutes, the clear wine-red solution was transferred to visking tubing (2.5 cm diameter) and dialysed for 12 hours against 0.01 sodium acetate buffer solution. The dialysate was examined and if turbid, centrifuged again at 27,000 g for 20 minutes. The clear preparation was transferred to sterile plastic stoppered tubes (10 ml) and stored at $-10°$ C prior to use. Enzyme preparations stored frozen in this manner exhibited no significant decrease in DHFR activity after 12 months.

B.2. Preparation of reagent solutions 0.15 M Phosphate buffer (pH 7.0) was used for all DHFR assays and was prepared by dissolving potassium dihydrogen orthophosphate (10.21 g) in water (c.a. 300 ml), adjusting the solution to pH 7.0 with potassium hydroxide, and diluting to 500 ml with water. The buffer was kept at 4° C to prevent bacterial growth and discarded after 3 days.

2-Mercaptoethanol solution (0.25 M) was prepared by dissolving 2-mercaptoethanol (1.75 ml) in water (to 100 ml) and the solution was stored in the dark at 4° C prior to use.

A solution of dihydrofolate (1 mg.ml$^{-1}$, 2 mM) was prepared immediately before use by suspending dihydrofolate in 0.23 M 2-mercaptoethanol solution and adding 1M-sodium hydroxide solution dropwise with vigorous agitation until dissolution had occurred. The solution was maintained at 0° C.

An aqueous solution of NADPH (2 mg.ml$^{-1}$, 2.0 mM) was prepared immediately prior to use and again maintained at 0° C.

B.3 Assay for inhibitor activity

The spectrophotometric assay was carried out with a Cary Model 16KC spectrophotometer fitted with a thermostatted rotating cell compartment capable of accommodating 5 sample and 5 reference cuvettes. Reaction rates were recorded on a Varian Model G2500 chart recorder, at a chart speed of 1 cm.min$^{-1}$ and a full scale deflection of 0.1 absorbance units, and the cuvettes were read sequentially at 10 second time intervals. Plastic disposable cuvettes were used throughout.

The assay was carried out as follows: NADPH (0.1 ml) and the enzyme preparation (0.1 ml) were incubated at 30° C for 5 minutes in phosphate buffer (total volume 1.9 ml). The reaction was initiated by addition of dihydrofolate (0.1 ml) and monitored by following the decrease in absorbance at 340 nm. Parallel assays were implemented where the reaction mixture contained 0.1 ml of the inhibitor at the required concentration and the volume of buffer was adjusted accordingly to give a final volume of 2 ml after addition of dihydrofolate.

Reference cuvettes were set up containing NADPH, buffer, inhibitor if appropriate and dihydrofolate, but without enzyme (Table A).

observed decrease in activity in the presence of inhibitor was expressed as a percentage of the uninhibited enzyme activity.

Activity against DHFR was initially measured at a final inhibitor concentration of $2.5\times10^{-5}$ M, in duplicate. Compounds producing an inhibition of less than 50% at this concentration were considered to be inactive. The remaining inhibitors were selected for $I_{50}$ determinations and inhibitory activity was evaluated in duplicate at a minimum of four inhibitor concentrations, from which the $I_{50}$ value was determined by a graphical method.

Compounds selected for inhibition constant ($K_I$) determinations were assayed following an identical method to that described above except that inhibitory activity was measured at a minimum of ten inhibitor concentrations, again in duplicate, from which the appropriate $K_I$ values were determined by a Zone B analysis. A $K_m$ value of 0.2 μM for dihydrofolate (S. Webber and J. M. Whiteley, Arch, Biochem. Biophys., 1985, 236 681) was adopted for the calculation of $K_I$.

Some results are shown in Tables I and II.

TABLE I

Inhibition of rat liver DHFR[a]

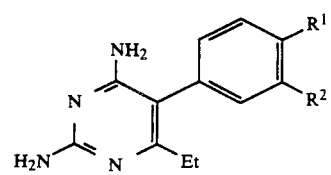

| R$^1$ | R$^2$ | Solvent | $I_{50}$(μM) |
|---|---|---|---|
| OMe | NO$_2$ | B | 0.18 |
| OEt | NO$_2$ | B | 0.14 |
| OBu$^n$ [b] | NO$_2$ | A | 0.06 |
| methylamino | NO$_2$ | B | 0.15 |
| dimethylamino | NO$_2$ | B | 0.25 |
| ethylamino | NO$_2$ | B | 0.16 |
| n-butylamino | NO$_2$ | B | 0.17 |
| benzylamino | NO$_2$ | B | 0.01 |
| N-methylbenzylamino | NO$_2$ | B | 0.01 |
| N-ethylbenzylamino | NO$_2$ | B | 0.02 |
| (±)α-methylbenzylamino | NO$_2$ | B | 0.18 |
| dibenzylamino | NO$_2$ | C | 0.26 |
| phenethylamino | NO$_2$ | C | 0.07 |
| metoprine (R$^1$ = R$^2$ = Cl, Et = Me) | | B | 0.10 |

Solvents: A = water, B = 0.1 M-hydrochloric acid, C = ethanol.
[a]Under identical assay conditions MTX gave an $I_{50}$ of 0.0019 μM.
[b]Compounds tested as ethanesulphonate salts.

TABLE A

DHFR assay: volumes of reagents, inhibitor and enzyme employed

| Nature of assay | NADPH[a] (ml) | Enzyme (ml) | Buffer (ml) | Inhibitor[b] (ml) | Dihydrofolate[c] (ml) | Final Volume (ml) |
|---|---|---|---|---|---|---|
| Uninhibited enzyme | 0.1 | 0.1 | 1.7 | — | 0.1 | 2 |
| Reference | 0.1 | — | 1.8 | — | 0.1 | 2 |
| Inhibited enzyme | 0.1 | 0.1 | 1.6 | 0.1 | 0.1 | 2 |
| Reference | 0.1 | — | 1.7 | 0.1 | 0.1 | 2 |

[a]$1\times10^{-4}$ M final concentration (saturating)
[b]The highly colored nature of several inhibitors necessitated the use of a reference cuvette
[c]$1\times10^{-4}$ M final concentration Enzyme activity was estimated from the slope of the change of absorbance with time and this was arbitrarily designated as 100% for the uninhibited enzyme. The

TABLE II

Kinetic data for selected diaminopyrimidine DHFR inhibitors against rate liver DHFR

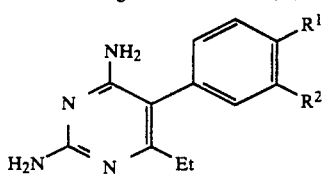

| R$^1$ | R$^2$ | K$_i$(nM) |
|---|---|---|
| n-butylamino[b] | NO$_2$ | 0.19 ± 0.05[a] |
| n-butoxy | NO$_2$ | 0.08 ± 0.06 |
| N-methylbenzylamino | NO$_2$ | 0.009 ± 0.002 |
| N-ethylbenzylamino | NO$_2$ | 0.04 ± 0.03 |
| Metoprine | K$_i$(nM) | 0.12 ± 0.04 |

($R^1 = R^2 = Cl$, Et = Me)

[a]95% confidence limits.
[b]Tested as ethanesulphonate salt.

In vitro cytotoxicity studies

Cultures of L1210 murine leukaemia cells were grown as a suspension in RPMI 1640 medium (with 25 mM hepes and L-glutamine) and 10% horse serum (Gibco Ltd., Paisley Scotland). Cells were seeded routinely every 72 hours at $10^4$ cells.ml$^{-1}$ and counted as $10^6$ cells.ml$^{-1}$ prior to each experiment and counts were performed following incubation (5% CO$_2$ in air at full humidity) for 72 hours at 37° C, with the appropriate concentration of drug. Generally incubations were carried out in duplicate and the increase in cell number in the presence of inhibitor after 72 hours was expressed as a percentage of the control cell count. Some results are shown in Table III. Further results are shown in Table IV.

TABLE III

Cytotoxicity of selected diaminopyrimidines against L1210 cells in vitro

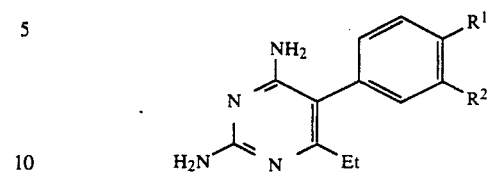

| R$^1$ | R$^2$ | IC$_{50}$(μM)[a] |
|---|---|---|
| n-butylamino | NO$_2$ | 0.2 |
| benzylamino | NO$_2$ | <0.001 |

[a]Drug concentration necessary to reduce the 72 hour cell count to 50% of control.

TABLE IV

In vitro activity of new diaminopyrimidines against rat liver dihydrofolate reductase and L1210 cells

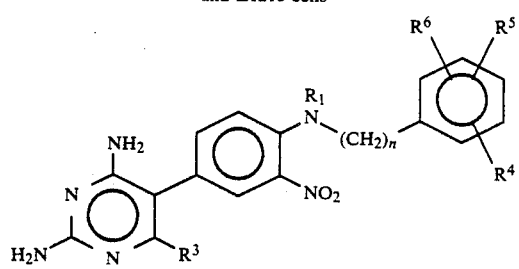

| Compound | R$_1$ | R$^4$(R$^5$ = R$^6$ = H) (R$^3$ = Et) | I$_{50}$(M) | Ki (M) | IC$_{50}$(L1210 cells) (M) |
|---|---|---|---|---|---|
| (15) | Me | 4-CO$_2$Me | 1 × 10$^{-8}$ | — | 1 × 10$^{-7}$ |
| (16) | Me | 4-CO$_2$(CH$_2$)$_2$OEt | 1.5 × 10$^{-9}$ | — | 4 × 10$^{-8}$ |
| (17) | Me | 4-OMe | 3.8 × 10$^{-7}$ | 1.6 × 10$^{-9}$ | 7 × 10$^{-8}$ |
| (18) | H | 4-OMe | 2.1 × 10$^{-8}$ | 8.8 × 10$^{-11}$ | 5 × 10$^{-8}$ |
| (19) | Me | 4-CONHMe | 9.1 × 10$^{-10}$ | 3.5 × 10$^{-13}$ | 2.5 × 10$^{-8}$ |
| (20) | Me | 4-CO$_2$H(H$_2$O) | 1 × 10$^{-9}$ | 4.0 × 10$^{-13}$ | 1.5 × 10$^{-8}$ |
| metoprine | | | 1 × 10$^{-7}$ | 1.2 × 10$^{-10}$ | |

Antitumor Screening

The results of preliminary in vivo screening against the P388 lymphocytic leukaemia in mice are shown below in Table V.

TABLE V

Antitumor activity for diaminopyrimidines against the P388 leukaemia[a]

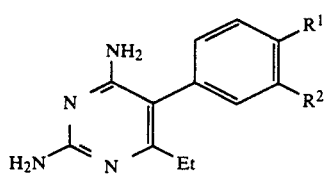

| R$^1$ | R$^2$ | Optimum Dose (mg·kg$^{-1}$) | Optimum[b] T/C (%) | NCI Status |
|---|---|---|---|---|
| OMe | NO$_2$ | 120 | 189 | ++ |
| methylamino | NO$_2$ | 100 | 182 | ++ |
| dimethylamino | NO$_2$ | 100 | 145 | + |
| n-butylamino | NO$_2$ | 240 | 206 | ++ |
| benzylamino | NO$_2$ | 240 | 126 | + |
| N-methylbenzylamino | NO$_2$ | 480 | 205 | ++ |
| N-ethylbenzylamino | NO$_2$ | 200 | 144 | + |
| (±)α-methylbenzylamino | NO$_2$ | 30 | 132 | + |
| phenethylamino | NO$_2$ | 200 | 142 | + |
| Metoprine | — | 50 | 140 | + |

TABLE V-continued

Antitumor activity for diaminopyrimidines against the P388 leukaemia[a]

[structure: pyrimidine with NH2, H2N-N=, attached to phenyl with R1, R2 substituents, and =CH-Et]

| R[1] | R[2] | Optimum Dose (mg·kg$^{-1}$) | Optimum[b] T/C (%) | NCI Status |
|---|---|---|---|---|
| (R[1] = R[2] = Cl, Et = Me) | | | | |

[a] All compounds administered to mice as free bases via intraperitoneal route according to NCI protocols.

By way of further example, the results of preliminary in vivo screening of Compounds (19), (20), (23), (25) and (28) against the M5076 reticulum cell sarcoma in mice are shown in Tables VI to X.

TABLE VI

In vivo activity of Compound (19) against the M5076 reticulum cell sarcoma in mice.
Tumor: implanted intramuscularly on day 1
Drug: in 10% DMSO/arachis oil administered daily for 17 days by intraperitoneal route.

| Dose (mg/kg/day) | Tumor volumes (mm$^3$): days after tumor implantation | | | | T/C × 100* |
|---|---|---|---|---|---|
| | 12 | 16 | 20 | 24 | |
| 12.5 | NM | NM | NM | 443 | 15 |
| 6.25 | NM | NM | 256 | 823 | 30 |
| 3.125 | NM | 246 | 457 | 1047 | 41 |
| 1.5 | NM | 420 | 670 | 1546 | 59 |
| 0.75 | 308 | 702 | 1174 | 1802 | 67 |
| Control | 522 | 1062 | 1822 | 2740 | 100 |

*Test/Control assessed at day 24
NM = not measurable

TABLE VII

In vivo activity of Compound (20) against the M5076 reticulum cell sarcoma in mice.
For details of tumor and drug administration see results on Compound (19).

| Dose (mg/kg/day) | Tumor volumes (mm$^3$): days after tumor implantation | | | | T/C × 100 |
|---|---|---|---|---|---|
| | 12 | 16 | 20 | 24 | |
| 12.5 | 347 | 836 | 1324 | 2704 | 100 |
| 6.25 | 369 | 786 | 1247 | 2442 | 89 |
| 3.125 | 422 | 954 | 1653 | 2861 | 107 |
| 1.5 | 409 | 1008 | 1943 | 3097 | 115 |
| 0.75 | 354 | 1046 | 1740 | 2707 | 100 |
| Control | 522 | 1062 | 1822 | 2740 | 100 |

TABLE VIII

In vivo activity of Compound (23) against the M5076 reticulum cell sarcoma in mice.
For details of tumor and drug administration see results on Compound (19).

| Dose (mg/kg/day) | Tumor volumes (mm$^3$): days after tumor implantation | | | | T/C × 100 |
|---|---|---|---|---|---|
| | 12 | 16 | 20 | 24 | |
| 50 | NM | NM | NM | NM | <8 |
| 25 | NM | NM | NM | NM | <8 |
| 12.5 | NM | NM | 216 | 395 | 16 |
| 6.25 | NM | 256 | 385 | 851 | 36 |
| 3.125 | 216 | 498 | 858 | 1173 | 48 |
| Control | 511 | 1000 | 2086 | 2483 | 100 |

TABLE IX

In vivo activity of Compound (25) against the M5076 reticulum cell sarcoma in mice.
For details of tumor and drug administration see results on Compound (19).

| Dose (mg/kg/day) | Tumor volumes (mm$^3$): days after tumor implantation | | | | T/C × 100 |
|---|---|---|---|---|---|
| | 12 | 16 | 20 | 24 | |
| 50 | Dead | — | — | — | — |
| 25 | NM | 180 | 426 | 514 | 20 |
| 12.5 | NM | 198 | 385 | 641 | 24 |
| 6.25 | NM | 270 | 704 | 1099 | 44 |
| 3.125 | 238 | 596 | 1581 | 1881 | 76 |
| Control | 511 | 1000 | 2086 | 2483 | 100 |

TABLE X

In vivo activity of Compound (28) against the M5076 reticulum cell sarcoma in mice.
For details of tumor and drug administration see results on Compound (19).

| Dose (mg/kg/day) | Tumor volumes (mm$^3$): days after tumor implantation | | | | T/C × 100 |
|---|---|---|---|---|---|
| | 12 | 16 | 20 | 24 | |
| 50 | Dead | — | — | — | — |
| 25 | NM | NM | NM | NM | <8 |
| 12.5 | NM | NM | NM | 265 | 12 |
| 6.25 | NM | NM | NM | 454 | 20 |
| 3.125 | NM | 291 | 627 | 948 | 40 |
| Control | 511 | 1000 | 2086 | 2483 | 100 |

We claim:

1. A compound of structural formula I, in the form of either the free base or a pharmaceutically acceptable acid addition salt thereof:

[structure I: pyrimidine with NH2, H2N-N, attached to phenyl with R1, R2, and R3 substituent]

wherein
R[1] is a benzyloxy group or is a mono-substituted or disubstituted amino group —NR$_1$R$_2$ wherein R$_1$ and R$_2$ are independently:
  hydrogen, an alkyl group of 1–6 carbon atoms, or a phenalkyl group of which the alkyl moiety has 1–6 carbon atoms;
  with the proviso that both R$_1$ and R$_2$ are not hydrogen;
R[2] is nitro group; and
R[3] is an alkyl group of 1 to 6 carbons.

2. A compound as claimed in claim 1, wherein R[1] is benzyloxy.

3. A compound as claimed in claim 1, wherein R[1] is —NHMe, —NHEt, NHBu$^n$, —NHCH$_2$CH$_2$Ph, —NHCH$_2$Ph, —NMeCH$_2$Ph, —N(CH$_2$Ph)$_2$, —NEtCH$_2$Ph, or —NHCH(Me)Ph.

4. A compound as claimed in claim 1 wherein R[3] is methyl or ethyl.

5. A compound as claimed in claim 1 which is one of the following:
 (1) 2,4-Diamino-5-(4-methylamino-3-nitrophenyl)-6-ethylpyrimidine, or an acid addition salt thereof;
 (2) 2,4-Diamino-5-(4-ethylamino-3-nitrophenyl)-6-ethylpyrimidine, or an acid addition salt thereof;

(3) 2,4-Diamino-5-(4-dimethylamino-3-nitrophenyl)-6-ethylpyrimidine, or an acid addition salt thereof;
(4) 2,4-Diamino-5-(4-n-butylamino-3-nitrophenyl)-6-ethylpyrimidine, or an acid addition salt thereof;
(5) 2,4-Diamino-5-(4-benzylamino-3-nitrophenyl)-6-ethylpyrimidine, or an acid addition salt thereof;
(6) 2,4-Diamino-6-ethyl-5-(4-N-methylbenzylamino-3-nitrophenyl)pyrimidine, or an acid addition salt thereof;
(7) 2,4-Diamino-6-ethyl-5-(4-N-ethylbenzylamino-3-nitrophenyl)pyrimidine, or an acid addition salt thereof;
(8) 2,4-Diamino-5-(4-dibenzylamino-3-nitrophenyl)-6-ethylpyrimidine, or an acid addition salt thereof;
(9) 2,4-Diamino-6-ethyl-5-(4-(±)-α-methylbenzylamino- 3-nitrophenyl)pyrimidine, or an acid addition salt thereof;
(10) 2,4-Diamino-6-ethyl-5-(3-nitro-4-phenethylaminophenyl)pyrimidine, or an acid addition salt thereof; and
(11) 2,4-Diamino-5-(4-N-methylbenzylamino-3-nitrophenyl)-6-methylpyrimidine, or an acid addition salt thereof.

6. A compound as claimed in claim 1 in the form of an acid addition salt derived from an acid selected from the group comprising:
hydrochloric, hydrobromic, sulphuric, nitric, isethionic, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic.

7. A compound according to claim 1 which is selected from the group consisting of:
2,4-Diamino-5-(4-N-methylbenzylamino-3-nitrophenyl)-6-methylpyrimidine ethanesulphonate salt; and 2,4-Diamino-5-(4-N-methylbenzylamino-3-nitro-phenyl)-6-ethylpyrimidine ethanesulphonate salt.

8. A compound of formula IA or a pharmaceutically acceptable acid addition salt thereof;

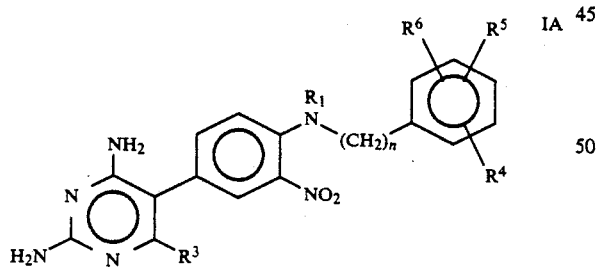

wherein: n is 1–6; $R_1$ represents hydrogen or alkyl; $R^4$, $R^5$ and $R^6$, which may be identical or different, each represent hydrogen, alkyl, alkoxy, halo, nitro, perfluoroalkyl, a group of formula —$CO_2R^a$ wherein $R^a$ represents hydrogen, alkyl or alkoxyalkyl, or a group of formula —$CONR^bR^c$ wherein $R^b$ and $R^c$ which may be identical or different each represent alkyl, or wherein one of $R^b$ and $R^c$ is hydrogen and the other is alkyl; and
$R^3$ represents alkyl, alkyl in each instance, alone or in combined form containing 1–6 carbons.

9. A compound as claimed in claim 8 wherein $R^3$ is methyl or ethyl.

10. A compound as claimed in claim 8 in the form of an acid addition salt derived from an acid selected from the group consisting:
hydrochloric, hydrobromic, sulphuric, nitric, isethionic, phosphoric, maleic, salicyclic, p-toluenesulphonic, tartaric, citric, lactobionic, formic, malonic, pantothenic, succinic, naphthalene-2-sulphonic, benzenesulphonic, methanesulphonic and ethanesulphonic.

11. A compound according to claim 8 selected from the group consisting of:
2,4-Diamino-6-ethyl-5-(4-{N-[4-methoxy-carbonylbenzyl]-N-methylamino]-3-nitrophenyl}pyrimidine, or an acid addition salt thereof;
2,4-Diamino-6-ethyl-5-(4-{N-methylamino}-3-nitrophenyl-pyrimidine, or an acid addition salt thereof;
2,4-Diamino-6-ethyl-5-{4-3-nitrophenyl}pyrimidine, or an acid addition salt thereof;
2,4-Diamino-6-ethyl-5-{4-3-nitrophenyl}pyrimidine, or an acid addition salt thereof;
2,4-Diamino-6-ethyl-5-(4-{N-[4-N-methyl-carbamoyl)benzyl]-carboxybenzyl-N-methylamino]-N-methylamino}-3-nitrophenyl)pyrimidine, or an acid addition salt thereof;
2,4-Diamino-6-ethyl-5-{4-3-nitrophenyl}pyrimidine monohydrate;
2,4-Diamino-5-[4-(2-chlorobenzylamino)-3-nitrophenyl]-6-ethylpyrimidine, or an acid addition salt thereof;
2,4-Diamino-5-[4-(4-chlorobenzylamino)-3-nitrophenyl]-6-ethylpyrimidine, or an acid addition salt thereof;
2,4-Diamino-5-[4-(3,4-dichlorobenzylamino)-3-nitrophenyl]-6-ethylpyrimidine, or an acid addition salt thereof;
2,4-Diamino-5-[4-(4-fluorobenzylamino)-3-nitrophenyl]-6-ethylpyrimidine, or an acid addition salt thereof;
2,4-Diamino-5-[4-(4-methylbenzylamino)-3-nitrophenyl]-6-ethylpyrimidine, or an acid addition salt thereof;
2,4-Diamino-5-[4-(3,4-dimethoxybenzylamino)-3-nitrophenyl]-6-ethylpyrimidine, or an acid addition salt thereof;
2,4-Diamino-5-[4-(2,4,6-trimethoxybenzylamino)-3-nitrophenyl]-6-ethylpyrimidine, or an acid addition salt thereof;
2,4-Diamino-5-[3-nitro-4-(4-trifluoromethylbenzylamino)phenyl]-6-ethylpyrimidine, or an acid addition salt thereof; and
2,4-Diamino-6-ethyl-5-(4-{N-[4-fluorobenzyl]-N-methylamino}-3-nitrophenyl)pyrimidine, or an acid addition salt thereof.

12. A compound of formula IA:

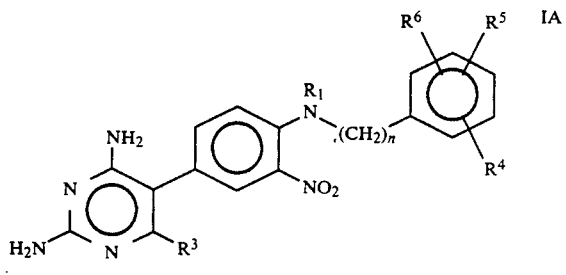

in the form of the free base or a pharmaceutically acceptable acid addition salt or hydrate thereof, wherein the substituents correspond to one of the following:

| | | | | | | |
|---|---|---|---|---|---|---|
| (a) | $R^4$ = 4-CO$_2$Me | $R^5$ = H | $R^6$ = H | $R^3$ = Et | $R_1$ = Me | n = 1 |
| (b) | $R^4$ = 4-CO$_2$(CH$_2$)$_2$OEt | $R^5$ = H | $R^6$ = H | $R^3$ = Et | $R_1$ = Me | n = 1 |
| (c) | $R^4$ = 4-OMe | $R^5$ = H | $R^6$ = H | $R^3$ = Et | $R_1$ = Me | n = 1 |
| (d) | $R^4$ = 4-OMe | $R^5$ = H | $R^6$ = H | $R^3$ = Et | $R_1$ = H | n = 1 |
| (e) | $R^4$ = 4-CONHMe | $R^5$ = H | $R^6$ = H | $R^3$ = Et | $R_1$ = Me | n = 1 |
| (f) | $R^4$ = 4-CO$_2$H | $R^5$ = H | $R^6$ = H | $R^3$ = Et | $R_1$ = Me | n = 1 |
| (g) | $R^4$ = 4-Cl | $R^5$ = H | $R^6$ = H | $R^3$ = Et | $R_1$ = H | n = 1 |
| (h) | $R^4$ = 4-Me | $R^5$ = H | $R^6$ = H | $R^3$ = Et | $R_1$ = H | n = 1 |
| (i) | $R^4$ = 4-F | $R^5$ = H | $R^6$ = H | $R^3$ = Et | $R_1$ = H | n = 1 |
| (j) | $R^4$ = 4-OMe | $R^5$ = 3-OMe | $R^6$ = H | $R^3$ = Et | $R_1$ = H | n = 1 |
| (k) | $R^4$ = 2-Cl | $R^5$ = H | $R^6$ = H | $R^3$ = Et | $R_1$ = H | n = 1 |
| (l) | $R^4$ = 4-Cl | $R^5$ = 3Cl | $R^6$ = H | $R^3$ = Et | $R_1$ = H | n = 1 |
| (m) | $R^4$ = 2-OMe | $R^5$ = 4-OMe | $R^6$ = 6-OMe | $R^3$ = Et | $R_1$ = H | n = 1 |
| (n) | $R^4$ = 4-CF$_3$ | $R^5$ = H | $R^6$ = H | $R^3$ = Et | $R_1$ = H | n = 1 |
| (o) | $R^4$ = 4-F | $R^5$ = H | $R^6$ = H | $R^3$ = Et | $R_1$ = Me | n = 1. |

13. A composition for inhibiting dehydrofolate reductase comprising an effective amount of a compound of the formula:

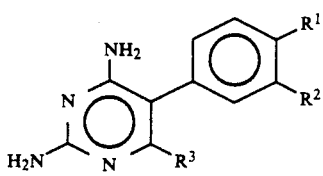

wherein $R^1$
  $R^1$ is an alkoxy group of 1–6 carbon atoms; an aralkoxy group which is benzyloxy; or a substituted amino group —NR$_1$R$_2$ wherein R$_1$ and R$_2$ are independently:
    hydrogen, an alkyl group of 1–6 carbon atoms, or a phenylalkyl group of which the alkyl moiety has 1–6 carbon atoms;
  with the proviso that both R$_1$ and R$_2$ are not hydrogen, R$^2$ is a nitro group and R$^3$ is an alkyl of 1 to 6 carbons, or pharmaceutically acceptable acid addition salt thereof, together with a pharmaceutically acceptable carrier.

14. A composition according to claim 13 in dosage unit form.

15. A method of inhibiting dihydrofolate reductase which comprises administering to a host in need of such inhibition, an inhibiting amount of a compound of the formula:

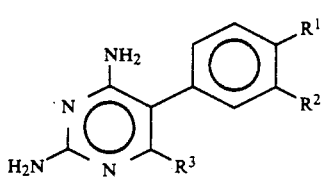

wherein $R^1$
  $R^1$ is an alkoxy group of 1–6 carbon atoms; an aralkoxy group which is benzyloxy; or a substituted amino group —NR$_1$R$_2$ wherein R$_1$ and R$_2$ are independently;
    hydrogen, an alkyl group of 1–6 carbon atoms, or a phenylalkyl group of which the alkyl moiety has 1–6 carbon atoms;
  with the proviso that both R$_1$ and R$_2$ are not hydrogen, R$^2$ is a nitro group and R$^3$ is an alkyl of 1 to 6 carbons or pharmaceutically acceptable acid addition salt.

* * * * *